(12) United States Patent
Ma et al.

(10) Patent No.: US 8,592,227 B2
(45) Date of Patent: Nov. 26, 2013

(54) HYBRID QUANTUM DOT/PROTEIN NANOSTRUCTURE, METHODS OF MAKING, AND METHODS OF USE THEREOF

(75) Inventors: Nan Ma, Mountain View, CA (US); Jianghong Rao, Sunnyvalle, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 138 days.

(21) Appl. No.: 13/068,174

(22) Filed: May 4, 2011

(65) Prior Publication Data

US 2011/0278554 A1 Nov. 17, 2011

Related U.S. Application Data

(60) Provisional application No. 61/330,931, filed on May 4, 2010.

(51) Int. Cl.
*H01L 21/00* (2006.01)

(52) U.S. Cl.
USPC .................. 438/1; 257/40; 257/E51.045

(58) Field of Classification Search
USPC .................. 257/40, E51.045; 438/1
See application file for complete search history.

(56) References Cited

U.S. PATENT DOCUMENTS

2011/0315927 A1* 12/2011 Tulsky et al. .......... 252/301.6 R

* cited by examiner

*Primary Examiner* — Marvin Payen
(74) *Attorney, Agent, or Firm* — Thomas Horstemeyer, LLP

(57) ABSTRACT

Embodiments of the present disclosure include hybrid quantum dot/protein nanostructure, hybrid quantum dot/protein nanostructure systems, methods of using hybrid quantum dot/protein nanostructures, and the like.

11 Claims, 8 Drawing Sheets

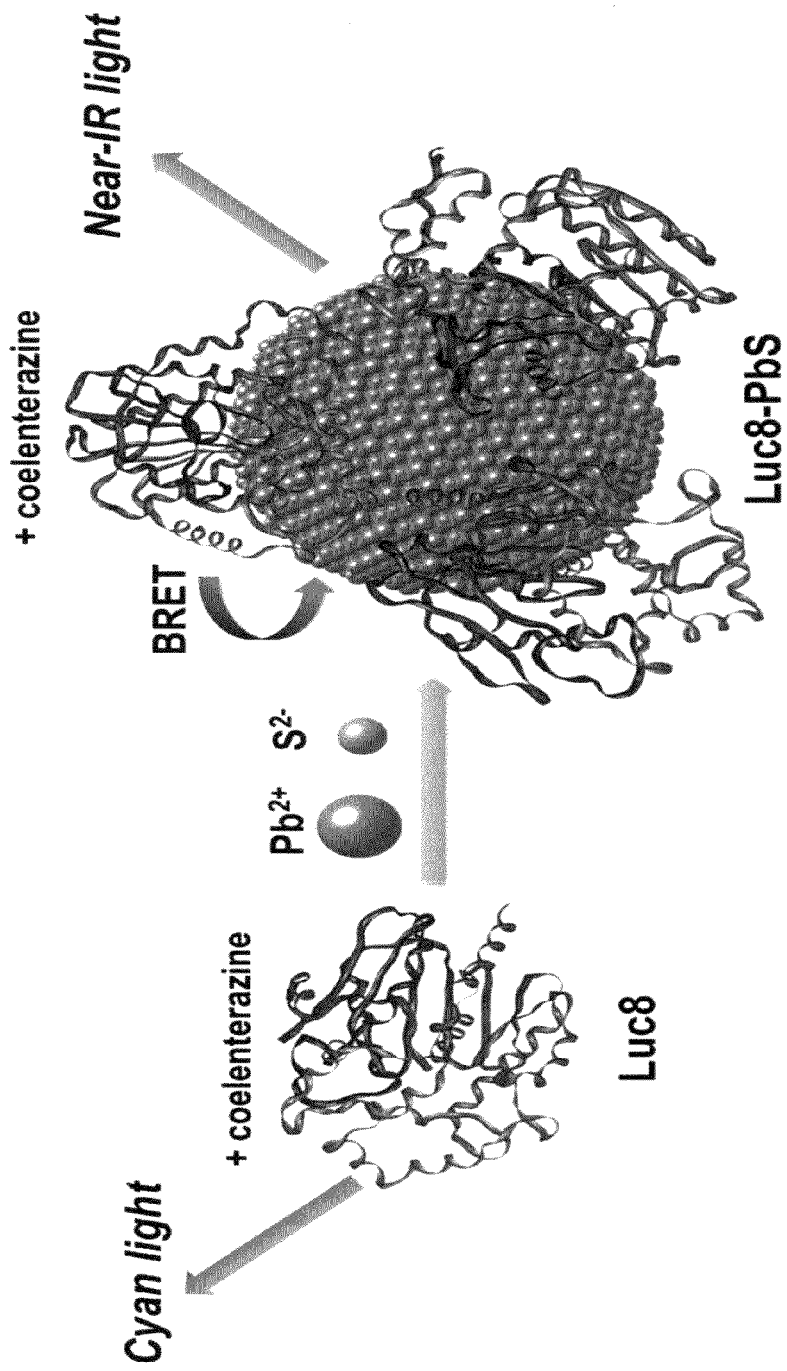
FIG. 1.1

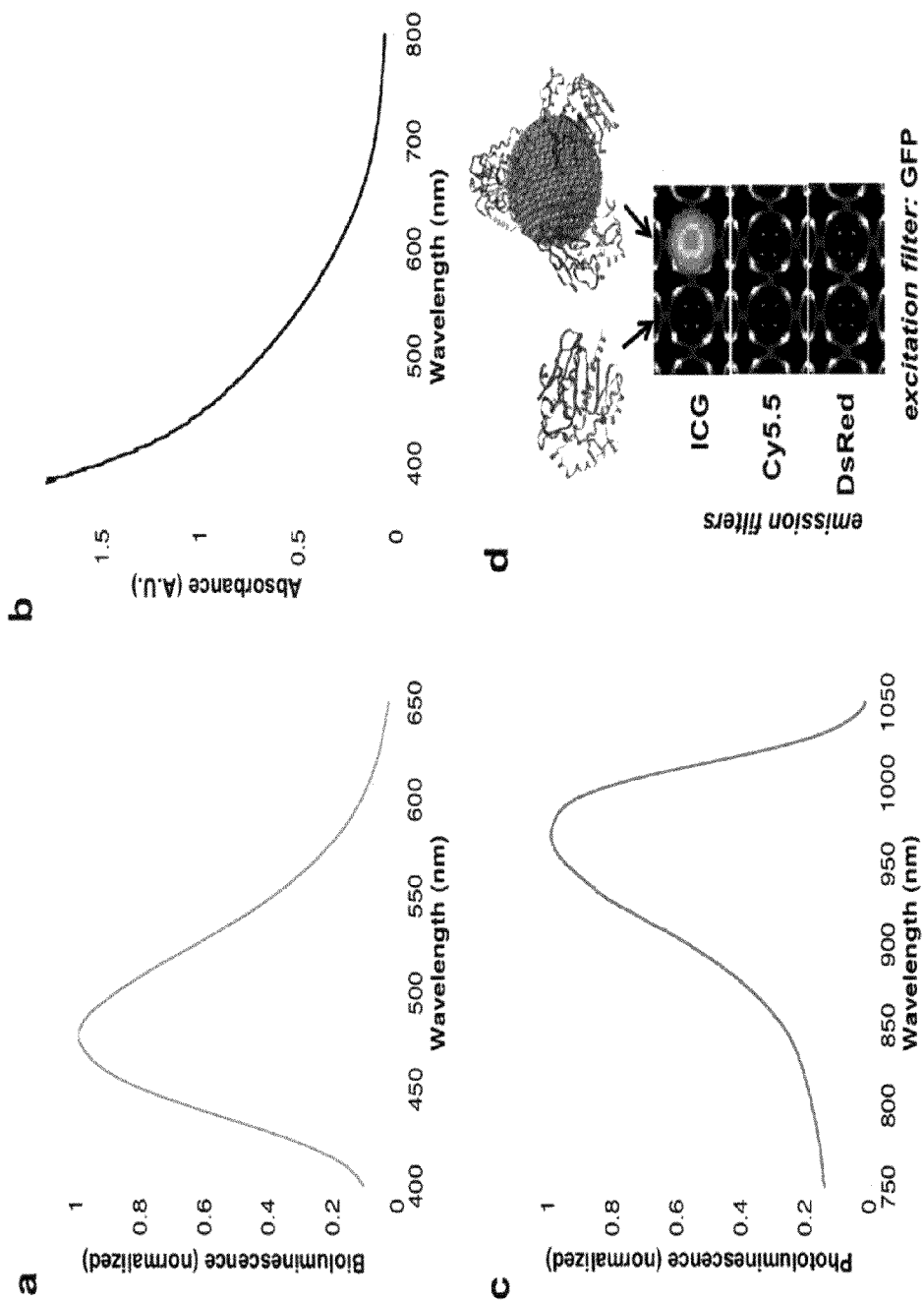
FIG. 1.2

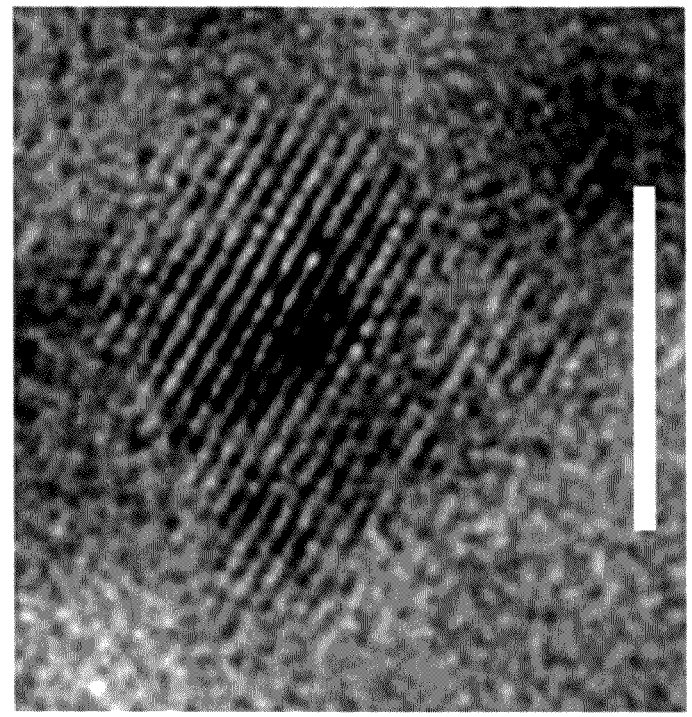
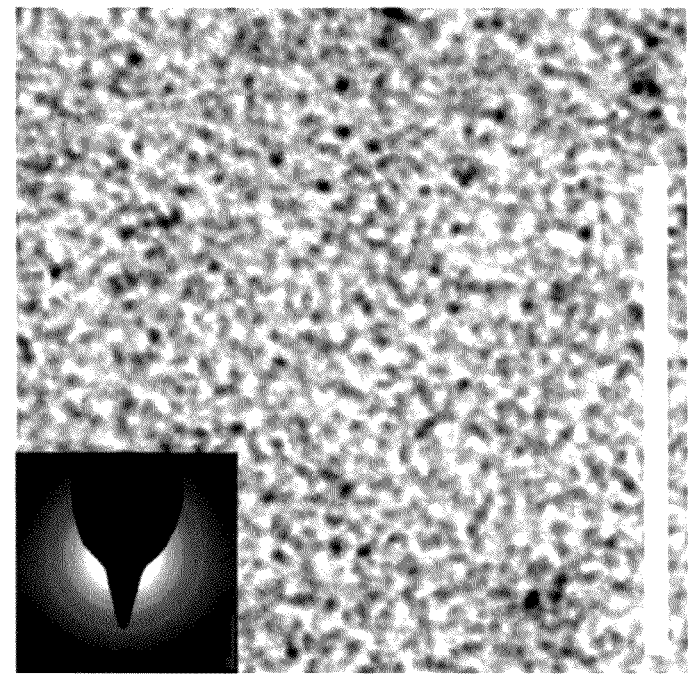
FIG. 1.3

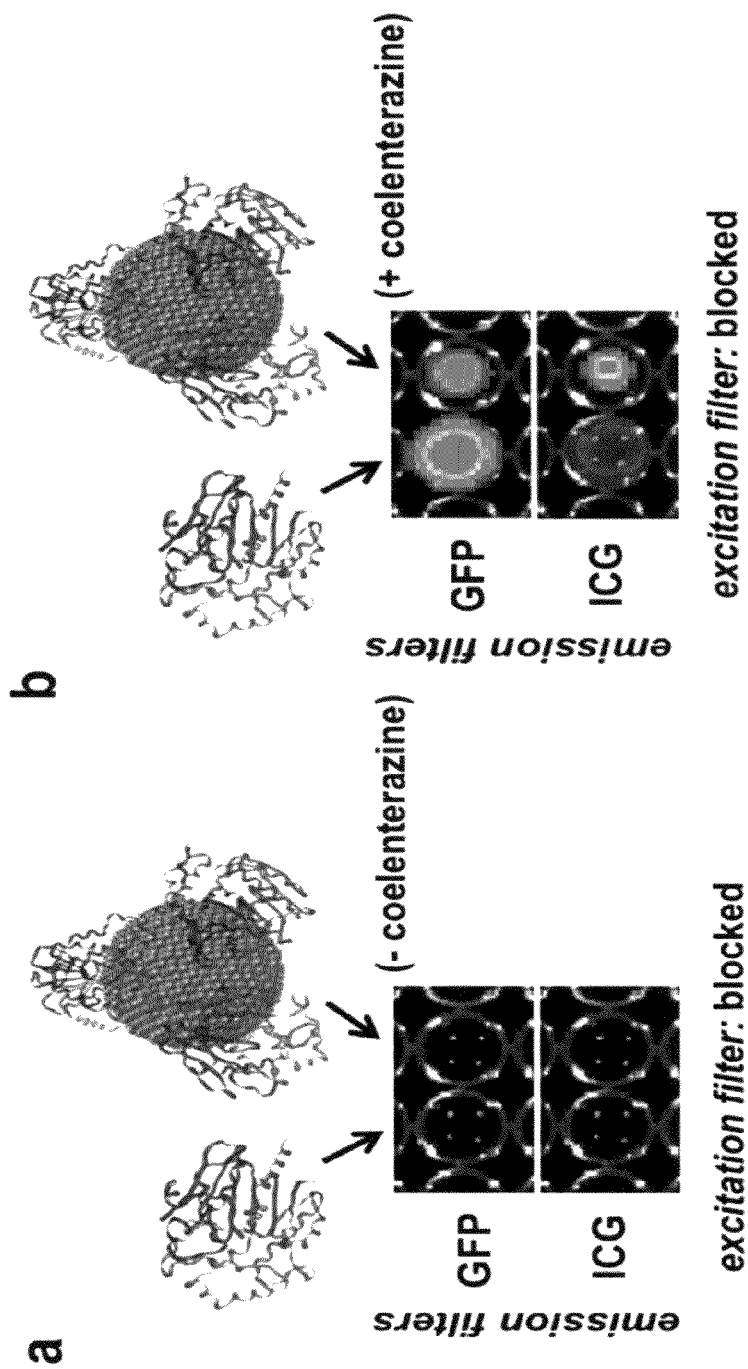
FIG. 1.4

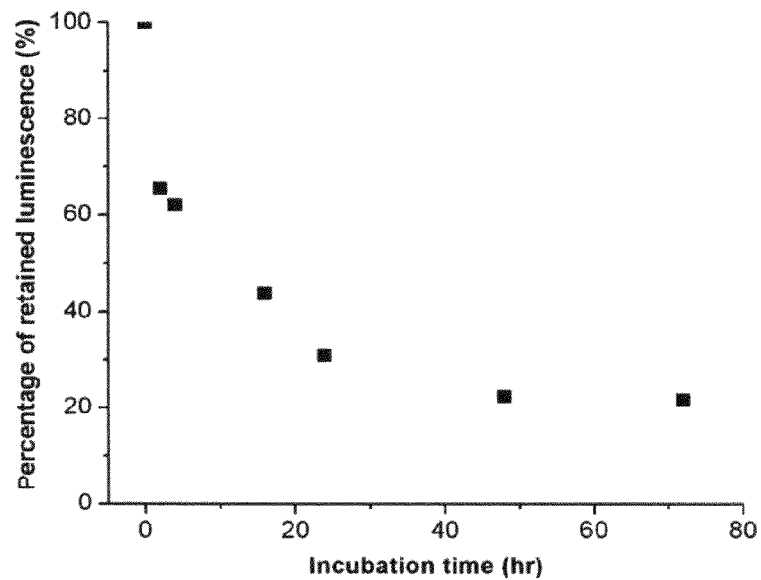
FIG. 1.5
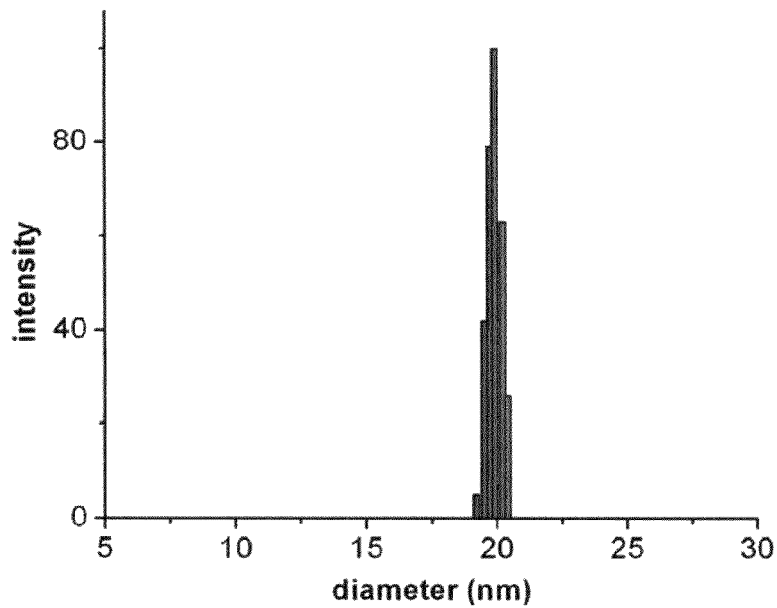
FIG. 1.6

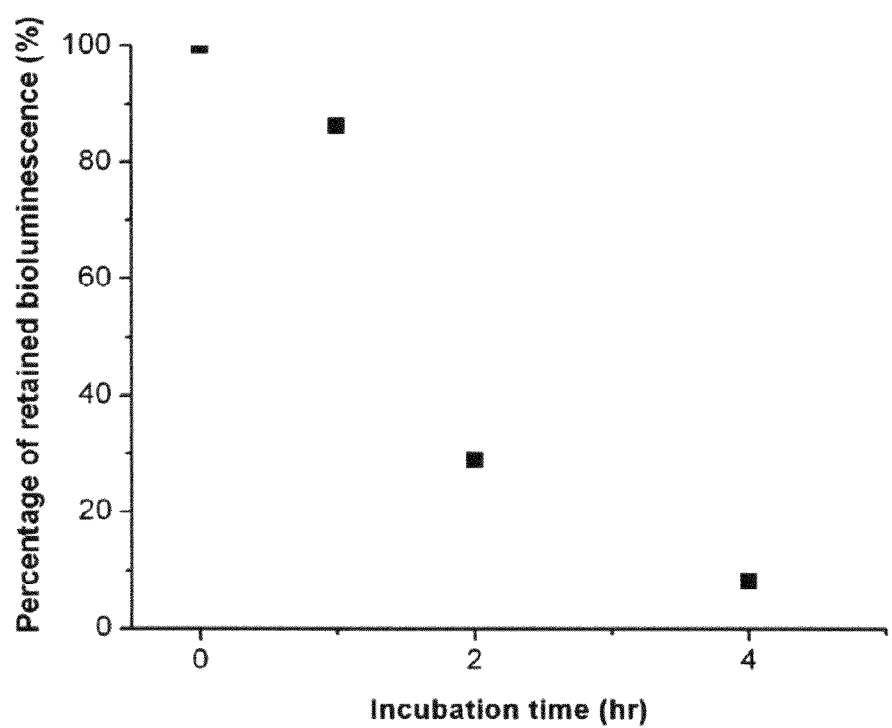
FIG. 1.7

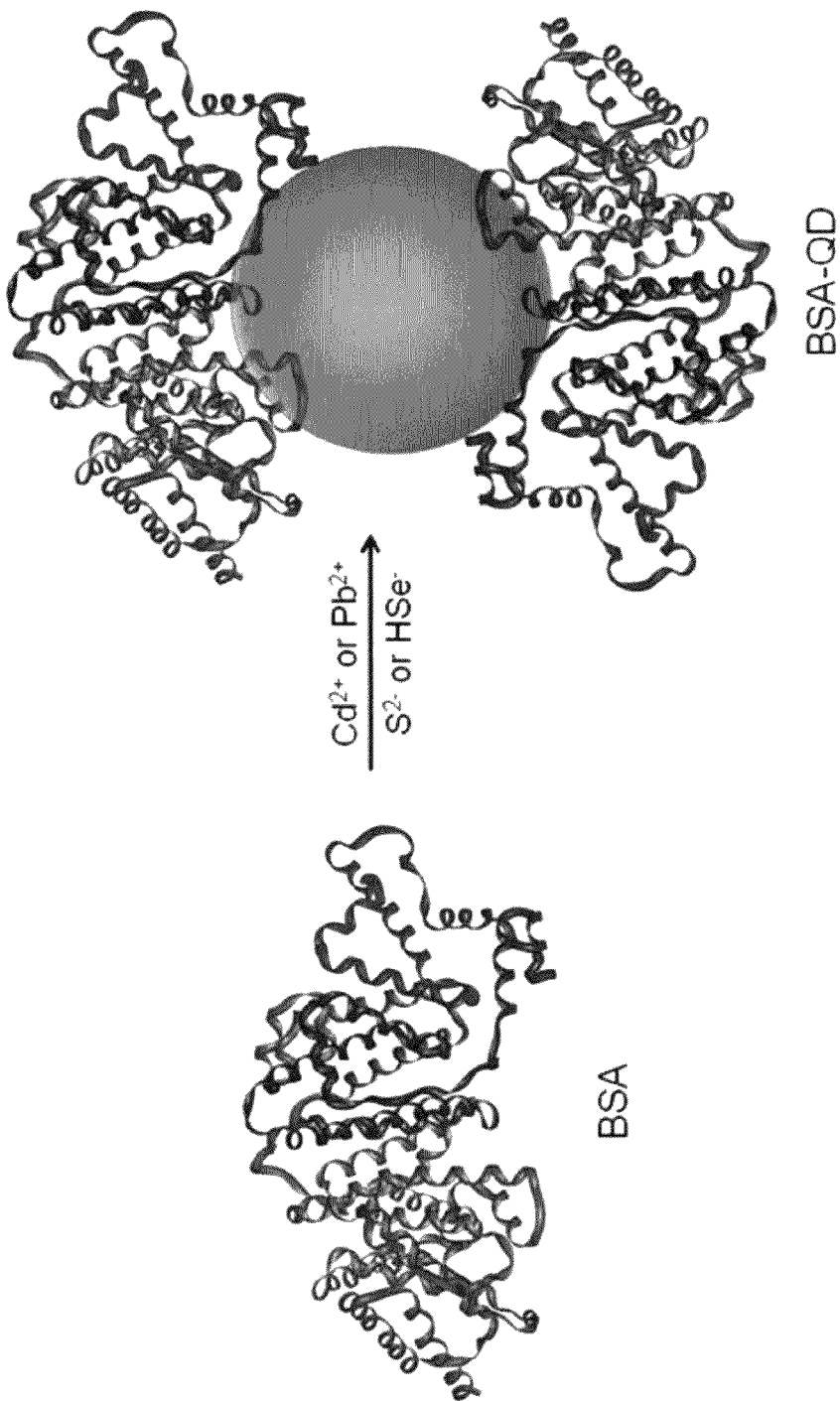
FIG. 2.1

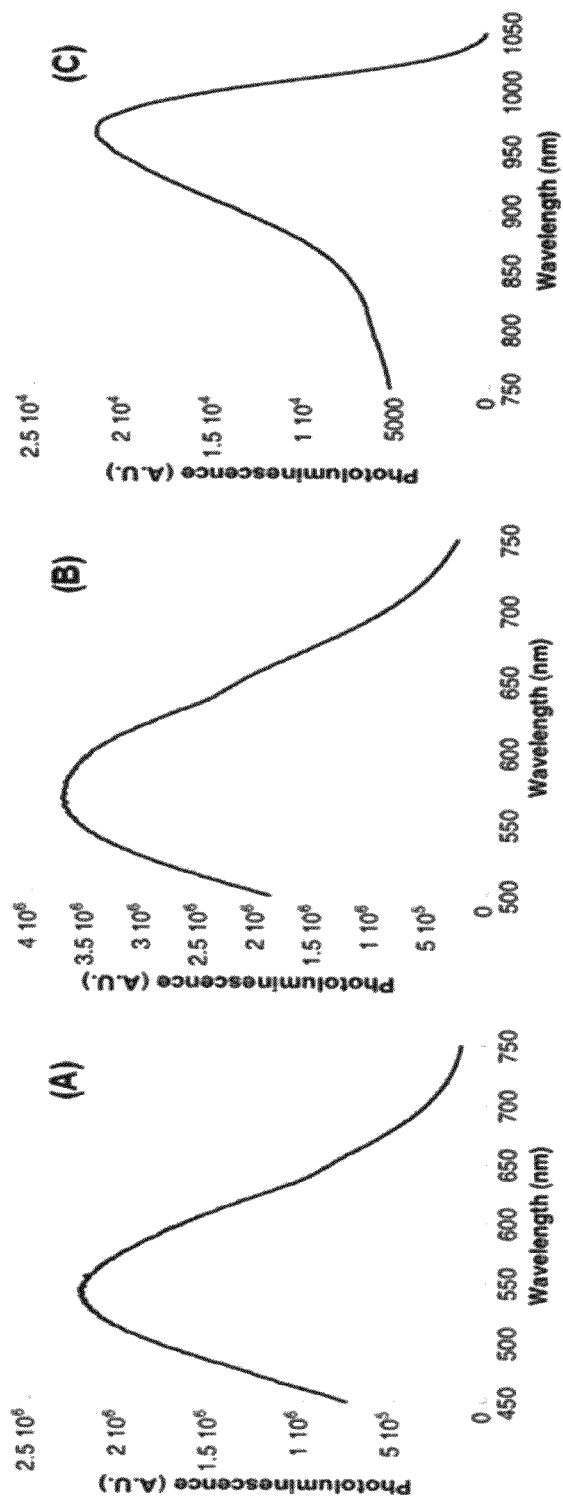
FIG. 2.2

HYBRID QUANTUM DOT/PROTEIN NANOSTRUCTURE, METHODS OF MAKING, AND METHODS OF USE THEREOF

CROSS-REFERENCE TO RELATED APPLICATIONS

This application claims priority to U.S. Provisional Patent Application Ser. No. 61/330,931, entitled "HYBRID QUANTUM DOT/PROTEIN NANOSTRUCTURE, METHODS OF MAKING, AND METHODS OF USE THEREOF" filed on May 4, 2010, which is hereby incorporated by reference.

STATEMENT REGARDING FEDERALLY SPONSORED RESEARCH OR DEVELOPMENT

This invention(s) was made with government support under Grant No.: 1R01CA135294-01 and 1U54CA119367-01 awarded by the National Cancer Institute. The government has certain rights in the invention(s).

BACKGROUND

The biomineralization processes use biomolecules to mediate the growth of inorganic structures in living organisms with distinct functions such as mollusks protection, tissue scaffolding and hardening, iron storage, and metal detoxification. The mild condition and high efficiency of biomineralization process have inspired researches to mimic it in vitro using a variety of biomolecules including proteins, nucleic acids, and polysaccharides to build functional inorganic materials. Biomolecules used in most studies merely serve as stabilizers or scaffolds to achieve bottom-up control of the properties of inorganic materials. Synthesis of dual functional bio-inorganic hybrid nanostructures directed by active enzymes remains little explored.

SUMMARY

Embodiments of the present disclosure include hybrid quantum dot/protein nanostructure, hybrid quantum dot/protein nanostructure systems, methods of using hybrid quantum dot/protein nanostructures, and the like.

One exemplary method of making a hybrid quantum dot/protein nanostructure, among others, includes: introducing a first precursor compound to a bioluminescence protein in a solution, wherein the precursor compound includes a first atom, wherein the bioluminescence protein bonds to a plurality of first atoms to form first atom-bioluminescence protein complexes; and introducing a second precursor compound to the solution including the first atom-bioluminescence protein complexes to form the hybrid quantum dot/protein nanostructure, wherein the second precursor compound includes a second atom, wherein the first atom and the second atom interact to form a quantum dot core, wherein the quantum dot core has a plurality of bioluminescence proteins each bonded to a plurality of first atoms.

One exemplary hybrid quantum dot/protein nanostructure system, among others, includes: a hybrid quantum dot/protein nanostructure and a bioluminescence initiating compound, wherein the hybrid quantum dot/protein nanostructure includes at least one bioluminescence protein bonded directly with a first atom of a core of a quantum dot, wherein when the bioluminescence protein and the bioluminescence initiating compound interact they are adapted to produce a bioluminescence energy, and wherein the quantum dot is adapted to emit a fluorescence energy in response to the non-radiative transfer of the bioluminescence energy from the bioluminescence protein to the quantum dot.

One exemplary nanostructure, among others, includes: a hybrid quantum dot/protein nanostructure including at least one bioluminescence protein bonded directly with a first atom of a core of a quantum dot.

Other compositions, methods, features, and advantages of this disclosure will be or become apparent to one with skill in the art upon examination of the following drawings and detailed description. It is intended that all such additional compositions, methods, features, and advantages be included within this description, be within the scope of this disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure.

FIG. 1.1 illustrates a schematic illustration of NIR light emitting luciferase via biomineralization.

FIG. 1.2 illustrates the characterization of Luc8 and Luc8-PbS complex. (a) Bioluminescence spectrum of Luc8 in the presence of coelenterazine. (b) Absorption spectrum of PbS QDs. (c) Fluorescence spectrum of Luc8-PbS QDs (excitation: 480 nm). (d) Imaging Luc8-PbS complex by IVIS Imaging System (with light excitation).

FIG. 1.3 illustrates low (a) and high (b) magnification TEM images of Luc8-PbS QDs; scale bars: 200 nm (a) and 5 nm (b). Inset: selected area diffraction (SAD) of QDs.

FIG. 1.4 illustrates the luminescence of Luc8 and Luc8-PbS complex in the absence (a) and presence (b) of coelenterazine (without excitation).

FIG. 1.5 illustrates the stability of Luc8-PbS QDs in 50 mM Tris (pH 7.5) measured by QD photoluminescence.

FIG. 1.6 illustrates the hydrodynamic sizes of Luc8-PbS complex measured by dynamic light scattering. The mean diameter is 19.9 nm.

FIG. 1.7 illustrates the stability of Luc8 protein within the Luc8-PbS complex.

FIG. 2.1 illustrates a schematic illustration of BSA-templated QD synthesis.

FIG. 2.2 illustrates photoluminescence spectra of BSA-QDs: (A). BSA-CdS QDs; (B) BSA-CdSe QDs; and (C) BSA-PbS QDs.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature. In particular, See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

"Bioluminescent protein" refers to a protein capable of acting on a bioluminescent initiator molecule substrate to generate bioluminescence.

"Bioluminescent initiator molecule" is a molecule that can react with a bioluminescent donor protein to generate bioluminescence.

Bioluminescence (BL) is defined as emission of light by living organisms that is well visible in the dark and affects visual behavior of animals (See e.g., Harvey, E. N. (1952). Bioluminescence. New York: Academic Press; Hastings, J. W. (1995). Bioluminescence. In: Cell Physiology (ed. by N. Speralakis). pp. 651-681. New York: Academic Press; Wilson, T. and Hastings, J. W. (1998). Bioluminescence. Annu Rev Cell Dev Biol 14, 197-230). Bioluminescence does not include so-called ultra-weak light emission, which can be detected in virtually all living structures using sensitive luminometric equipment (Murphy, M. E. and Sies, H. (1990), Meth. Enzymol. 186, 595-610; Radotic, K, Radenovic, C, Jeremic, M. (1998), Gen Physiol Biophys 17, 289-308). Bioluminescence also does not include weak light emissions, which most probably does not play any ecological role, such as the glowing of bamboo growth cone (Totsune, H., Nakano, M., Inaba, H. (1993), Biochem. Biophys. Res Comm. 194, 1025-1029). Bioluminescence also does not include emission of light during fertilization of animal eggs (Klebanoff, S. J., Froeder, C. A., Eddy, E. M., Shapiro, B. M. (1979), J. Exp. Med. 149, 938-953; Schomer, B. and Epel, D. (1998), Dev Biol 203, 1-11). Each of the citations referenced above are incorporated herein by reference.

As used herein, the term "host", "subject", or "patient" includes humans, mammals (e.g., cats, dogs, horses, etc.), and the like. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. The term "living host" refers to host noted above that are alive. The term "living host" refers to the entire host and not just a part excised (e.g., a liver or other organ) from the living host.

General Discussion

Embodiments of the present disclosure include hybrid quantum dot/protein nanostructure, hybrid quantum dot/protein nanostructure systems, methods of using hybrid quantum dot/protein nanostructures, and the like.

Embodiments of the method for making hybrid quantum dot/protein nanostructure are advantageous for at least the reason that the method is simple and can be conducted in a simple "one-pot" synthesis, although the synthesis could be conducted in multiple reaction vessels if desired. In general, the method includes using bioluminescence proteins as biotemplates to form quantum dot cores, where bioluminescence proteins are bonded to atoms of the quantum dot core. Although the bioluminescence proteins are bonded to the quantum dot core atoms, the bioluminescence proteins retain their bioluminescent properties after the quantum dot core is formed. As described in more detail below, the bioluminescence proteins bond to a plurality of first atoms (e.g., from a first precursor compound, where the atom can be a cation such as $Pb^{2+}$) and facilitates the heterogeneous nucleation in a solution. Subsequently, a second atom (e.g., from a second precursor compound, where the atom can be an anion such as $S^{2-}$) is introduced to the complex and forms a quantum dot core having the bioluminescence proteins bonded to a plurality of the first atoms of the quantum dot core. Additional details are described in the Examples.

In general, embodiments of the present disclosure involve the non-radiative transfer of energy between a bioluminescence protein and a quantum dot core without external illumination. In general, the bioluminescence protein interacts with a bioluminescence initiating molecule to produce an emission. The non-radiative transfer of energy from the bioluminescence protein to the quantum dot core causes the quantum dot core to emit radiation at a different wavelength that can be detected and measured using an appropriate detection system. In other words, bioluminescence resonance energy transfer (BRET) can take place between the bioluminescence protein and the quantum dot core. In this regard, embodiments of the present disclosure do not need an external light source to produce an emission from the quantum dot core.

The hybrid quantum dot/protein nanostructure can be used to produce bioluminescent and/or fluorescent images. In addition, multiplexed imaging of one or more targets, can be performed by using a plurality of hybrid quantum dot/protein nanostructure where each conjugate includes a quantum dot core with distinct emission spectra.

It should also be noted that since the hybrid quantum dot/ protein nanostructure does not need an external illumination source, the sensitivity is increased because the background signal-to-noise ratio increases. It should also be noted that the endogenous chromophores in the imaged tissue emit radiation in response to an external illumination source, where such radiation would decrease the signal-to-noise ratio.

In addition, the hybrid quantum dot/protein nanostructures are distinguishable and can be individually detected. In this regard, the hybrid quantum dot/protein nanostructure can be modified so that the hybrid quantum dot/protein nanostructures interact with certain targets or target compounds (e.g., chemical and/or biological compounds or polymers such as biomolecules, proteins, DNA, RNA, and the like), which allows detection of the target molecules (e.g., in-vivo) thereby determining the area in which the target molecules are located, for example. In an embodiment, the target can include, but is not limited to, a compound, a polypeptide, a polynucleotide, an antibody, an antigen, a hapten, a cell type, a tissue type, an agent (as described below), and the like.

Embodiments of the disclosure can be used in applications such as the following: cellular studies, in vivo cell trafficking, stem cell studies, tumor imaging, biomolecule array systems, biosensing, biolabeling, gene expression studies, protein studies, medical diagnostics, diagnostic libraries, microfluidic systems, delivery vehicles, multiplex imaging of multiple events substantially simultaneously, and high throughput assays for drug screening. For example, the hybrid quantum dot/protein nanostructure in combination with spectral imaging can be used for multiplexed imaging and detection (in vitro or in vivo) of polynucleotides, polypeptides, and the like, in a system, a host or single living cell. The hybrid quantum dot/protein nanostructure can be used to detect (and visualize) and quantitate events in a system, a host or cell in in vitro as well as in in vivo studies, which decreases time and expenses since the same system can be used for cells and living organisms. For example, a drug being tested in a cell culture with the hybrid quantum dot/protein nanostructure can then also be tested in living subjects using the same self-illuminating quantum dot conjugates.

Embodiments of the disclosure can be used to non-invasively measure selected events or interactions, the presence or absence of an agent (e.g., chemical and/or biological compounds or polymers), and the like at a depth in an animal from about less than 6 centimeters (cm), less than about 5 cm, less than about 4 cm, less than about 3 cm, less than about 2 cm, and less than about 1 cm. For example, the hybrid quantum dot/protein nanostructure can be used to measure cellular events in deep tissue.

In particular, the hybrid quantum dot/protein nanostructure can be used in in vivo diagnostic and/or therapeutic applications such as, but not limited to, targeting diseases and/or conditions and/or imaging diseases and/or conditions. For example, one or more embodiments of the hybrid quantum dot/protein nanostructure can be used to identify the type of disease, locate the proximal locations of the disease, and/or deliver agents (e.g., drugs) to the diseased cells (e.g., cancer cells, tumors, and the like) in living animals.

As mentioned above, the hybrid quantum dot/protein nanostructure includes a bioluminescence protein and a quantum dot core. In the presence of the bioluminescence initiating molecule or compound, the bioluminescence initiating compound can react with the bioluminescence protein. The reaction causes the bioluminescence protein to emit bioluminescence energy. The non-radiative energy transfer from the bioluminescence protein to the quantum dot core can occur when there is an overlap (e.g., greater than 0.1%) between the emission and excitation spectra of the donor and acceptor molecules, respectively. It should be noted that the greater the overlap, the greater the efficiency. The energy is accepted by the quantum dot core, and then the quantum dot core emits fluorescent energy. The bioluminescence energy and/or the fluorescent energy can be detected and quantified in real time using an appropriate detection system (e.g., a photomultiplier tube in a fluorometer and/or a luminometer, for example).

In an embodiment, the hybrid quantum dot/protein nanostructure could be designed to degrade in the presence of certain agents. Therefore, the ratio of the bioluminescence energy and the fluorescent energy can be detected and quantified in real time to watch the hybrid quantum dot/protein nanostructure degrade. Thus, the presence of an agent (e.g., an agent present in a precancerous cell, cancer, and/or tumor, or some other disease) can be detected by observing the decay of the fluorescent energy emitted by the quantum dot core because the BRET between the quantum dot core and the bioluminescence protein is reduced and/or eliminated.

In an illustrative embodiment, the detection system used to measure the signal from the hybrid quantum dot/protein nanostructure includes, but is not limited to, a light tight module and an imaging device disposed in the light tight module. The imaging device can include, but is not limited to, a CCD camera and a cooled CCD camera. It should be noted that other detection systems can be used to detect the bioluminescence energy and/or the fluorescent energy, such as, but not limited to, a fluorometer, a luminometer, a multiple well microplate reader, and the like.

In an embodiment, the hybrid quantum dot/protein nanostructure can be detected in a system (e.g., a bioluminescence resonance energy transfer (BRET) system) using a detection system having a cooled charge-coupled device (CCD) camera, for example, capable of imaging low intensity of visible light ranges from 300 to 900 nm wavelength emitted from superficial and deep tissue structures of small living subjects.

Hybrid Quantum Dot/Protein Nanostructure

As indicated above, the hybrid quantum dot/protein nanostructure can include, but is not limited to, a bioluminescence protein and a quantum dot core. In an embodiment, the bioluminescence protein is bonded directly to a first atom at the quantum dot surface. In an embodiment, the bioluminescence protein is bonded directly to two or more first atoms at the quantum dot surface. The terms "bond" or "bonded" refer to the direct chemical association (e.g., covalently or ionically) of the bioluminescence protein to a plurality of first atoms of the quantum dot core, where the bonds are established during the nucleation of the quantum dot core by the first precursor compound and the bioluminescence. In an embodiment, the bond between/among the bioluminescence protein and the first atom is a covalent bond.

In general, a hybrid quantum dot/protein nanostructure can include a number of bioluminescence proteins bonded to one or more first atoms on the surface of the quantum dot core. The number of bioluminescence proteins per quantum dot core can be controlled, at least in part, by controlling the preparation conditions, the first and second precursor compounds, the type of bioluminescence protein, and the like. The number of bioluminescence proteins per quantum dot core may be about 1 to 100, 1 to 75, 1 to 50, 1 to 30, 1 to 20, and 1 to 10. In an embodiment, the more bioluminescence proteins per quantum dot core, the higher the emission intensity. Therefore, the number of bioluminescence proteins per quantum dot can be used to control the intensity of the quantum dot emission. Additional details about the bioluminescence proteins and the quantum dot core are described below.

In an embodiment, the self-illuminating quantum dot conjugate or the bioluminescence protein and the quantum dot core can also include one or more types of agents bound (e.g., associated directly or indirectly) to the bioluminescence protein and/or the quantum dot core. The hybrid quantum dot/protein nanostructure or the bioluminescence protein and the quantum dot core can include one or more agents that can be used to enhance the interaction of the hybrid quantum dot/protein nanostructure with the host or subject. The agent can have an affinity for a target such as, but not limited to, a compound, a polypeptide, a polynucleotide, an antibody, an antigen, a hapten, a cell type, a tissue type, and the like. In an embodiment, the agent may be an antigen specific for an antibody that corresponds to a certain disease or condition. In another embodiment, the agent may be a first protein specific for another protein. In another embodiment, the agent may be a polynucleotide sequence specific for a complementary polynucleotide sequence. In another embodiment, the agent can undergo a chemical, biological, and/or physical change, where the changed agent can have an affinity for another agent or target.

The agent can include, but is not limited to, polypeptides (e.g., protein such as, but not limited to, an antibody (monoclonal or polyclonal)), nucleic acids (both monomeric and oligomeric), polysaccharides, sugars, fatty acids, steroids, purines, pyrimidines, drugs (e.g., small compound drugs), ligands, or combinations thereof. In an embodiment, the agent has an affinity for functional groups, compounds, cells, tissue, and the like, associated with a disease or condition. The agent can have an affinity for one or more targets.

In another embodiment, the agent can make the hybrid quantum dot/protein nanostructure or the bioluminescence protein and the quantum dot core bio-compatible. In other words, the hybrid quantum dot/protein nanostructure can include a bio-compatibility compound. The bio-compatibility compound can include compounds such as, but not limited to, polyethylene glycol; polypropylene glycol 500, dextran, and derivatives thereof. The bio-compatibility compound can be attached directly or indirectly with the quantum dot core and/or an agent bound to the quantum dot core.

Thus, the agent can be selected so that the hybrid quantum dot/protein nanostructure can be used to image and/or diagnose the presence or absence of the compounds, polypeptides, polynucleotides, antibodies, antigens, haptens, cell types, tissue, types, and the like, associated with a disease or condition, or related biological activities.

In addition, the agent can also include, but is not limited to, a drug, a therapeutic agent, radiological agent, a small molecule drug, and combinations thereof, that can be used to treat the target molecule and/or the associated disease and condition of interest. The drug, therapeutic agent, and radiological agent can be selected based on the intended treatment as well as the condition and/or disease to be treated. In an embodiment, the hybrid quantum dot/protein nanostructure can include two or more agents used to treat a condition and/or disease.

In an embodiment, the hybrid quantum dot/protein nanostructure or the bioluminescence protein and the quantum dot core can include at least two different types of agents, one being a targeting agent that targets certain cells or compounds associated with a condition and/or disease, while the second agent is a drug used to treat the disease. In this manner, the hybrid quantum dot/protein nanostructure acts as a detection component, a delivery component to the cells of interest, and a delivery component for the treatment agent. The detection of the hybrid quantum dot/protein nanostructure can be used to ensure the delivery of the nanostructure to its intended destination as well as the quantity of hybrid quantum dot/protein nanostructure delivered to the destination.

Methods of Making Quantum Dot/Protein Nanostructure

As noted above, embodiments of the method for making hybrid quantum dot/protein. nanostructure can be conducted in a simple "one-pot" synthesis. In other words, the reagents can be mixed in a single reaction vessel to produce the final product (e.g., hybrid quantum dot/protein nanostructure). In general, the bioluminescence proteins are used as bio-templates to form quantum dot cores, where the bioluminescence proteins are bonded to the first atoms on the surface of the quantum dot core and where the bioluminescence proteins retain their bioluminescent properties. The term "bio-template" refers to biomolecules such as proteins, peptides, nucleic acids, and polysaccharides that can efficiently chelate metal ions and initiate the heterogeneous nucleation to allow the nanoparticle to grow along or within the biomolecules.

Initially, a first precursor compound is introduced to a bioluminescence protein in a solution (e.g., aqueous). The first precursor compound includes a first atom (e.g., $Pb^{2+}$, $Cd^{2+}$, $Zn^{2+}$, and the like). The first precursor compound can include compounds that include the first atom (e.g., which can include a cation) and dissociate in solution. In an embodiment, the first precursor compound can include lead acetate, lead nitrate, cadmium chloride, and zinc chloride. Additional first precursor compounds can be used as long as they provide a first atom that can bond to the bioluminescence protein and can be used to form a quantum dot core as described below. In general, the temperature of the solution can be about 4 to 30° C. and the pH of the solution can be about 7 to 10. The solution is incubated for about 5 to 10 min to allow the first atom to bond to the bioluminescence protein and facilitate the heterogeneous nucleation process. In an embodiment, the solution including the first atom-bioluminescence protein complexes is colorless and transparent.

Subsequently, a second precursor compound is introduced to the solution including the first atom-bioluminescence protein complexes to form the hybrid quantum dot/protein nanostructure. In an embodiment, the ratio of the first atom to the second atom present in the solution is about 1:1 to 4:1 or about 1:2. In an embodiment, the precursor concentrations are about 100 μM to 5 mM. The second precursor compound includes a second atom (e.g., $S^{2-}$, $Se^{2-}$, $Te^{2-}$, and the like). The second precursor compound can include compounds that include the second atom (e.g., which can include an anion), dissociate in solution, and can be used to form a quantum dot core as described below. In an embodiment, the second precursor compound can include sodium sulfide, sodium selenide, selenium powder, sodium telluride, and tellurium powder. In the case of selenium and tellurium powder, the powder can be converted to selenide ion ($Se^{2-}$) and telluride ion ($Te^{2-}$) by a reducing reagent such as sodium borohydride ($NaBH_4$). Additional second precursor compounds can be used as long as they provide a second atom that can interact with the first atom to form the quantum dot core. In general, the temperature of the solution can be about 4 to 30° C. and the pH of the solution can be about 7 to 10.

In an embodiment, after introducing the second precursor compound into the solution containing the first atom-bioluminescence protein complexes, the solution is immediately agitated on a vortex mixer for 10 to 20 seconds. In an embodiment, the solution color turns to yellow or brown during the agitation indicating the formation of quantum dots. The protein-quantum dot hybrid nanostructure are highly dispersed in the solution. The quantum dot core of the hybrid quantum dot/protein nanostructure has a plurality of bioluminescence proteins each bonded to at least one first atom. The size of quantum dot core can be about 1 to 40 nm or about 4 to 8 nm. Additional details are described in the Examples.

Quantum Dot Core

As indicated above, the hybrid quantum dot/protein nanostructure can include quantum dot cores such as, but not limited to, luminescent semiconductor quantum dot cores. The "core" is a nanometer-sized semiconductor. While any core of the BB-VIA, IIIA-VA, or IVA-VIA semiconductors can be used in the context of the present disclosure. A IIB-VIA semiconductor is a compound that contains at least one element from Group IIB and at least one element from Group VIA of the periodic table, and so on. For example, the core can be PbS, Au, CdS, CdSe, CdTe, ZnSe, ZnS, PbSe, or an alloy.

The core can include two or more elements. In one embodiment, the core is a IIB-VIA, IIIA-VA, or IVA-VIA semiconductor that ranges in size from about 1 nanometers (nm) to 40 nm, about 1 nm to 30, about 1 nm to 20 nm, about 1 nm to 10 nm. In another embodiment, the core is more preferably a IIB-VIA or VIA-VIA semiconductor and ranges in size from about 2 nm to 10 nm.

The wavelength emitted (i.e., color) by the quantum dot cores can be selected according to the physical properties of the quantum dot cores, such as the size and the material of the nanocrystal. Quantum dot cores are known to emit light from about 300 nm to 2000 nm (e.g., UV, near IR, and IR). The colors of the quantum dot cores include, but are not limited to, red, blue, green, and combinations thereof The color or the fluorescence emission wavelength can be tuned continuously. The wavelength band of light emitted by the quantum dot is determined by either the size of the core. The emission wavelength band can be tuned by varying the composition and the size of the quantum dot core.

The intensity of the color of the quantum dot cores can be controlled. For each color, the use of 10 intensity levels (0, 1, 2, . . . 9) gives 9 unique codes, because level "0" cannot be differentiated from the background. The number of codes increase exponentially for each intensity and each color used. For example, a three color and 10 intensity scheme yields 999 codes, while a six color and 10 intensity scheme has a theoretical coding capacity of about 1 million.

In general, it is more advantageous to use more colors, rather than more intensity levels, in order to increase the number of usable codes. The number of intensities is preferably from 1 to 20, more preferably about 1 to 10. The number of colors is preferably about 1 to 10 (e.g., 2-8), and more preferably, about 3 to 7. By the term "multicolor quantum dot," it is meant that more than one color of luminescent quantum dots is associated with the same agent. For example two hybrid quantum dot/protein nanostructures with different colored quantum dots are bound to the same agent, so that both emit radiation when in contact with the particular agent.

Bioluminescent Protein

As noted above, the quantum dot core of the hybrid quantum dot/protein nanostructure has a plurality of bioluminescent proteins each bonded to a plurality of first atoms. The polar and charged amino acid residues such as thiol, amine, and carboxyl group can bond to the metal cations (e.g., $Pb^{2+}$, $Cd^{2+}$, and $Zn^{2+}$) on quantum dot surface through coordinate covalent bonds or ionic bonds.

The bioluminescence protein can include, but is not limited to, luciferases, *Renilla* Luciferase, firefly Luciferase, aquorin, click beetle Luciferase, Gaussia Luciferase, horse radish peroxidase, and other bioluminescence proteins that can work with quantum dot cores and with methods of making hybrid quantum dot/protein nanostructure.

In an embodiment, the bioluminescence protein can include, but is not limited to, a *Renilla* Luciferase protein (as described herein and in the example) (Rluc, SEQ ID NO:1), a mutated *Renilla* Luciferase protein (as described herein and in the example) (Rluc8, SEQ ID NO:2), conservatively modified variants of each, and combinations thereof. The mutated *Renilla* Luciferase protein can include, but is not limited to, 8 mutations in the sequence, and these include A55T, C124A, 5130A, K136R, A143M, M185V, M253L, and S287L (e.g., as described herein and in the example). In addition, mutated *Renilla* Luciferase protein can include conservatively modified variants of one or more of these mutations as long as the conservatively modified variant retains the characteristics of the mutated *Renilla* Luciferase protein.

In an embodiment, when the bioluminescence protein is a mutated *Renilla* Luciferase protein, the bioluminescence sensitivity increase of about 20 to 60 fold or more and about 40 fold can be realized. Also in embodiments using the mutated *Renilla* Luciferase protein, the mutated *Renilla* Luciferase protein is more stable relative to other proteins.

In general, the mutated *Renilla* Luciferase protein is very stable. It has been shown that a C124A mutation increases the stability of RLuc. In order to further enhance the stability of RLuc, a number of mutations can be included in addition to the C124A mutation. The combination of 8 favorable mutations including C124A generated a mutant *Renilla* luciferase (RLuc8) that exhibited a greater than 150-fold stability improvement in murine serum when compared to native Rluc (<1 hr versus>100 hr) and increased the sensitivity of the system by about 20 to 60 fold and about 40 fold relative to native *Renilla* Luciferase. In addition to being more stable, RLuc8 also exhibited at least a 4-fold improvement in light output, along with a about 5 nm red shift to its emission spectrum with respect to the native Rluc. The *Renilla* Luciferase protein and the mutated *Renilla* Luciferase protein are described in more detail in the Examples and in Nature Biotechnology 2006 (So M-K, Xu C, Loening A M, Gambhir S S, Rao J. Self-illuminating quantum dot conjugates for in vivo imaging. *Nature Biotechnology* 2006; 24: 339-343.)

Bioluminescence Initiating Compound

As mentioned above, the hybrid quantum dot/protein nanostructure is used in conjunction with a bioluminescence initiating compound to produce a radiation emission that is absorbed by the quantum dot core. The bioluminescence initiating compound can include, but is not limited to, coelenterazine, analogs, and functional derivatives thereof, and D-luciferin analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp, coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750 and 5,874,304), which are incorporated herein by reference. In an embodiment, the bioluminescence initiating compound can be D-luciferine when the bioluminescence compound is firefly luciferase.

In general, coelenterazines are known to luminesce when acted upon by a wide variety of bioluminescent proteins, specifically luciferases. Coelenterazines disclosed in U.S. patent application Ser. No. 10/053,482, filed Nov. 2, 2001 (which is hereby incorporated by reference in its entirety), could be used as well. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997, which are incorporated herein by reference.

Methods of Use

As mentioned above, the present disclosure relates generally to methods for studying (e.g., detecting, localizing, or quantifying) cellular events, in vivo cell trafficking, stem cell studies, tumor imaging, biomolecule array systems, biosensing, biolabeling, gene expression studies, protein studies, medical diagnostics, diagnostic libraries, microfluidic systems, and delivery vehicles. The present disclosure also relates to methods for multiplex imaging of multiple events substantially simultaneously inside a subject (e.g., a host living cell, tissue, or organ, or a host living organism) using one or more hybrid quantum dot/protein nanostructure without the use of an external excitation source for the quantum dot.

In short, the hybrid quantum dot/protein nanostructure is introduced to the subject using known techniques. The hybrid quantum dot/protein nanostructure can also be labeled with one or more types of agents for the particular study (e.g., agents directed to cancer imaging and/or treatment), as mentioned above. In addition, a single agent can be associated with two or more types of hybrid quantum dot/protein nanostructure, where the hybrid quantum dot/protein nanostructure includes different quantum dot cores.

In an embodiment, at an appropriate time (e.g., before, after, or at the same time as the hybrid quantum dot/protein nanostructure), the bioluminescence initiating compound is introduced to the host living cell, tissue, or organ, or a host living organism. In an embodiment, the appropriate time may include a time frame to allow unassociated hybrid quantum dot/protein nanostructures to be sufficiently cleared from the appropriate area, region, or tissue of interest. The bioluminescence initiating compound can react with the bioluminescence protein. The reaction causes the bioluminescence protein to emit bioluminescence energy. The energy transfer from the bioluminescence protein to the quantum dot core can occur when there is an overlap between the emission and excitation spectra of the donor and acceptor molecules, respectively. The energy is accepted by the quantum dot core, and then the quantum dot core emits fluorescent energy. The bioluminescence energy and/or the fluorescent energy can be detected and quantified in real time using a detection system. The measured signal is or can be correlated to the feature being studied. In an embodiment, the detection of the bioluminescence energy and/or the fluorescent energy can be conducted after a sufficient time frame to allow unassociated hybrid quantum dot/protein nanostructure to be sufficiently cleared from the appropriate area, region, or tissue of interest.

Kits

This disclosure encompasses kits, which include, but are not limited to, hybrid quantum dot/protein nanostructure (e.g., optionally with one or more agents as described above), a bioluminescence initiating compound (optionally), and directions (written instructions for their use). The components listed above can be tailored to the particular cellular event being studied and/or treated (e.g., cancer, cancerous, or precancerous cells). The kit can further include appropriate buffers and reagents known in the art for administering various combinations of the components listed above to the host cell or host organism.

EXAMPLE

Now having described the embodiments of the hybrid quantum dot/protein nanostructure, methods of making, systems, and methods of use, in general, the examples as shown in the Attachments describe some additional embodiments of the hybrid quantum dot/protein nanostructure, methods of making, systems, and methods of use. While embodiments of hybrid quantum dot/protein nanostructure, methods of making, systems, and methods of use are described in connection with the examples and the corresponding text and figures, there is no intent to limit embodiments of the hybrid quantum dot/protein nanostructure, methods of making, systems, and methods of use to this description. On the contrary, the intent is to cover all alternatives, modifications, and equivalents included within the spirit and scope of embodiments of the present disclosure.

Example 1

Brief Introduction

A new strategy based on biomineralization is presented to rationally tune the emission wavelength of luciferase. In this study luciferase (Luc8) was used as a template to direct the synthesis of near infrared (NIR) light emitting PbS QDs at ambient conditions to form a Luc8-PbS complex. The as-synthesized PbS QDs exhibited photoluminescence in the range of 800 nm-1050 nm and the Luc8 enzyme remained active within the Luc8-PbS complex. Upon the addition of the substrate coelenterazine, the energy produced by Luc8 was transferred to PbS QDs non-radiatively via bioluminescence resonance energy transfer (BRET) and enabled the complex to emit NIR light. This is the first example describing how to form dual functional bio-inorganic hybrid nanostructures via bioactive enzyme-templated synthesis of inorganic nanomaterials.

Discussion

Luciferase is a class of bioluminescent proteins that convert chemical energy into light by oxidizing its substrate luciferin. The emissions of most natural and recombinant luciferases are normally in the visible region from blue to yellow and can be further tuned via bioluminescence resonance energy transfer (BRET) in living organisms or biomimetic systems.[1] Bioluminescence beyond the natural range especially in the near-infrared (NIR) region is highly desired for deep-tissue imaging yet difficult for protein or substrate engineering.[2] Inspired by the biomolecule-templated nanomaterial synthesis, we describe here a new strategy based on biominerization to generate NIR light emitting luciferase.

Biomolecules are effective ligands for inorganic nanomaterials with functional groups such as amine, thiol, and phosphate chelating metal ions and passivating nanoparticle surfaces post-synthesis.[3,4] In this work we use luciferase enzyme as the template to grow PbS QDs as a Luc-PbS hybrid nanostructure (Scheme 1 in FIG. 1.1). We expect that luciferase can act with dual functions for both QD growth and energy production. The addition of substrate (coelenterazine) initiates BRET and enables the Luc-PbS complex to emit NIR light. In the current study we select an eight-mutation variant of *Renilla reniformis* luciferase (Luc8) that possesses enhanced stability versus the wild-type luciferase.[5] The synthesis was initiated by incubating luciferase with lead acetate $(Pb(Ac)_2)$ at ambient conditions to allow the binding of $Pb^{2+}$ to Luc8 and facilitate the heterogeneous nucleation. Next, a sodium sulfide $(Na_2S)$ solution was quickly injected into the Luc8-$Pb^{2+}$ mixture followed by intense agitation to promote nanocrystal growth. A light brown solution was produced immediately after the introduction of $Na_2S$ and the resulting materials were stably dispersed in the solution with high solubility. In contrast, the reaction proceeded in the absence of Luc8 only produced large insoluble aggregates, which indicates that Luc8 is required for stabilizing PbS nanocrystals. We choose a $Pb^{2+}$ to $S^{2-}$ ratio of 2:1 for the synthesis given that excess metal ions are usually required for QD surface passivation and preservation of high quantum yield (QY). Different buffers including 1xPBS (pH 7.4), 50 mM Tris (pH 7.5), and pure $H_2O$ were tested for the synthesis. The PbS QDs with the highest luminescence intensity were produced in 50 mM Tris buffer. Those synthesized in pure $H_2O$ exhibited moderate luminescence. Interestingly, no luminescent materials were generated in 1xPBS which could interfere with the nanocrystal formation and quench their photoluminescence.[6] The luminescence of QDs is also dependent on the protein concentration, and as high as 0.5 mg/mL of Luc8 is required to synthesize luminescent product. The as-synthesized PbS QDs exhibit NIR luminescence with an emission peak in an approximate range of 800-1050 nm (FIG. 1.2c) with the QY of 3.6% that is comparable to other NIR QDs prepared in water phase.[7] The absorption spectrum of PbS QDs overlap well with the emission spectrum of Luc8 (FIG. 1.2), which is the prerequisite for BRET. Synthesis of PbS QDs with a different protein-bovine serum albumin as the template under the same condition produced the QDs with same emission spectrum and similar QY.

We further analyzed the luminescence of Luc8-PbS in a 96-well plate with an IVIS imager. GFP filter (445-490 nm) was used for excitation and three different band-pass emission filters were used: ICG (810-875 nm), Cy5.5 (695-770 nm), and DsRed (575-650 nm). As shown in FIG. 1.2d, the luminescence of PbS QDs was detected only via ICG filter, which is consistent with the emission spectrum of PbS QDs. No signal was detected from the control Luc8 alone. The stability of Luc8-PbS was tested at 37° C. over a time course of 72 hours (SI). No aggregates formed during the incubation but a slow decrease in luminescence intensity was observed, which is probably due to the QD surface oxidation.[8]

The size and morphology of as-synthesized Luc-PbS QDs were characterized using transmission electron microscopy (TEM). Monodisperse spherical nanoparticles can be easily identified with a mean diameter of ~4 nm (FIG. 1.3). The diffraction rings obtained by selected area diffraction (SAD) further confirms that the nanoparticles are crystalline materials (FIG. 1.3a inset). The lattice fringes of a single PbS QD can be clearly visualized in the high resolution TEM image (FIG. 1.3b). The mean hydrodynamic diameter of Luc8-PbS complex is 19.9 nm as measured by dynamic light scattering (SI).

Next, we proceeded to explore the BRET within the Luc8-PbS complex. The excess Luc8 in the Luc8-PbS solution was removed by filtering through Microcon YM-100 centrifugal device. The luminescence signals were monitored using an IVIS Imager. The excitation was blocked in order to monitor the bioluminescence signals. Two emission filters—GFP filter (515-575 nm) and ICG filter (810-875 nm) were used to detect the Luc8 bioluminescence and PbS luminescence, respectively. As expected, no signal was detected in the absence of coelenterazine (FIG. 1.4a); upon the addition of coelenterazine, bioluminescence signals were detected from Luc8-PbS under the GFP emission filter, confirming that the Luc8 remains active while passivating on PbS QD surface. The bioluminescence signal of Luc8 alone (left well in FIG. 1.4b) is stronger than that of Luc8-PbS likely because the energy is partially transferred to PbS QD non-radiatively. The NIR luminescence signal was detected only from Luc8-PbS QDs under ICG emission filter, confirming that BRET occurred. The BRET ratio between Luc8 and PbS QDs is 0.118 (see SI for details). The stability of Luc8 within the Luc8-PbS complex was further monitored (FIG. 1.7): 86% bioluminescence retained after one hour. Further decreases after prolonged incubation may be caused by the interactions between the nanoparticle and the protein which could promote protein conformation change and impair its catalytic activity.[9]

In summary, we report a new strategy to construct NIR light emitting luciferase via a biomineralization process. To the best of our knowledge, it is the first example of enzyme-templated synthesis of NIR QDs. The finding that luciferase remains active and enables BRET within the Luc8-PbS complex represents an important advance over previous templated nanomaterial synthesis in which the biomolecules are merely used as stabilizers whereas their biological functions are neglected. This study can be extended to other biomolecules and nanomaterials to generate dual functional nanostructures by integrating the functions of biomolecules and nanomaterials via a simple one-pot synthesis.

Supporting Information for Example 1

Experimental

Luc8 Expression and Purification

The expression plasmids were transformed into *E. coli* TOP 10 competent cells (Invitrogen). The transformed cells were grown in 1 L of LB media containing 100 µg/mL ampicillin at 37° C. and induced with 0.2% arabinose at the $OD_{600}$ of ~0.6. After 4 h induction at 37° C., the cells were harvested by centrifugation and frozen at –80° C. The cells were thawed in 10 mL of 20 mM Tris pH 7.5 containing 20 mM imidazole, 300 mM NaCl, and 1 mg/mL lysozyme. The resuspended cells were incubated for 30 min at room temperature and sonicated for 3 min. The lysates were clarified by centrifugation at 15000 rpm for 30 min at 4° C. The clarified supernatant containing expressed proteins was incubated with 1 mL of Ni—NTA agarose (Qiagen) at 4° C. for 1 h with gently shaking. The Ni—NTA agarose beads were washed with 100 mL of 20 mM Tris pH 7.5, 20 mM imidazole, 300 mM NaCl. His-tagged proteins were eluted with 5 mL of the same buffer containing 250 mM of imidazole. The eluted fractions were further purified using a PD-10 desalting column. The protein concentration was determined according to the absorbance at 280 nm with an extinction coefficient of 63495 $M^{-1}$ $cm^{-1}$. The Luc8 bioluminescence was measured upon the addition of 1 µg coelenterazine (Prolume).

PbS QDs Synthesis

All the solutions were freshly prepared prior to the synthesis. For a typical synthesis, 190 µL of 50 mM Tris (pH 7.5) containing 0.5 mg/mL Luc8 was mixed with 12 µL of 10 mM $Pb(CH_3COO)_2$ (Sigma) and incubated at room temperature for 5 min. Next, 6 µL of 10 mM $Na_2S$ (Sigma) was quickly injected into the solution followed by intense agitation on a vortex mixer for 10 seconds.

Optical Characterization of PbS QDs

The absorption spectrum of PbS QDs was recorded on an Agilent 8453 UV-Vis spectrometer. The emission spectrum of PbS QDs was measured using a FluoroLog-3 fluorometer conjugated to an InGaAs infrared detector with corrections. Cardiogreen was used as the standard for the QY determination. The QY was calculated according to the following equation:

$$\phi_x = \phi_s \left(\frac{A_s}{A_x}\right)\left(\frac{Int_x}{Int_s}\right)\left(\frac{\eta_x}{\eta_s}\right)^2$$

where $\phi$ is the quantum yield, Int is the area under the emission peak, A is absorbance at the excitation wavelength, and $\eta$ is the refractive index of the solvent. The subscripts s and x denote the respective values of the standard and QDs (The QY of cardiogreen is 1.3% in $H_2O$). Luminescence signals of PbS QDs were also monitored using the IVIS Imaging System (IVIS 109). Samples were placed in a 96-well plate and the photoluminescence was recorded using a GFP excitation filter and an ICG emission filter. For bioluminescence measurements, the excitation light was blocked and a GFP emission filter and an ICG emission filter were used to record the bioluminescence of Luc8 and PbS QDs, respectively.

Nanocharacterization of PbS QDs

Purified Luc8-PbS QDs (5 µL) were dropped on a 3 mm copper grid covered with a continuous layer of carbon film (Ted Pella). The grid was then dried in a vacuum desiccator for 2 hrs. The QDs were imaged under an FEI Tecnai G2 F20 transmission electron microscope operated at 200 kV. Dynamic light scattering was performed using a Brookhaven 90 plus nanosizer (FIG. 1.6).

Stability Test of PbS QDs

The Luc8-PbS QDs in 50 mM Tris (pH 7.5) were incubated at 37° C. over a 72 hour time course and aliquot solutions were taken out at each time point for luminescence measurement (FIG. 1.5).

Stability Test of Luc8 within Luc8-PbS Complex

The Luc8-PbS QDs in 50 mM Tris (pH 7.5) were incubated at 37° C. and aliquot solutions were taken out at different time points (0 hr, 1 hr, 2 hr, and 4 hr) for bioluminescence measurements (FIG. 1.7).

BRET Ratio Determination

The BRET ratio was calculated according to the following equation [ref: *FASEB J.* 2005, 19, 2017]:

$$BRET ratio = \frac{E_{ICG}(PbS) \times \frac{Int_1(PbS)}{Int_2(PbS)}}{E_{GFP}(Luc8) \times \frac{Int_1(Luc8)}{Int_2(Luc8)}}$$

where $E_{ICG}$(PbS) is the emission intensity of PbS QDs within the Luc8-PbS complex determined by IVIS imaging system using ICG emission filter, $E_{GFP}$(Luc8) is the bioluminescence intensity of Luc8 protein within the Luc8-PbS complex determined by IVIS imaging system using GFP emission filter. The emission intensities (photon/s/$cm^2$/sr) are obtained by drawing an ROI (region of interest) over each sample using the Live Image 3.0 software.

$$\frac{Int_1(PbS)}{Int_2(PbS)}$$

is the correction factor for PbS QDs, where $Int_1$(PbS) is the integrated area of the whole emission spectra of PbS QDs and $Int_2$(PbS) is the integrated area of the PbS QDs emission spectra within the wavelength range of the band pass ICG emission filter; similarly $$\frac{Int_1(Luc8)}{Int_2(Luc8)}$$

is the correction factor for Luc8 protein, where $Int_1$(Luc8) is the integrated area of the whole emission spectra of Luc8 and $Int_2$(Luc8) is the integrated area of Luc8 emission spectra within the wavelength range of the band pass GFP emission filter.

REFERENCES, EACH OF WHICH IS INCORPORATED HEREIN BY REFERENCE (1) (a) Xu, Y.; Piston, D. W.; Johnson, C. H. *Proc. Natl. Acad. Sci. USA* 1999, 96, 151. (b) So, M.-K.; Xu, C.; Loening, A. M.; Gambhir, S. S.; Rao, J. *Nat. Biotechnol.* 2006, 24, 339.

(2) Nakatsu, T.; Ichiyama, S.; Hiratake, J.; Saldanha, A.; Kobashi, N.; Sakata, K.; Kato, H. *Nature* 2006, 440, 372.
(3) Ma, N.; Sargent, E. H.; Kelley, S. O. *J. Mater. Chem.* 2008, 18, 954.
(4) Peelle, B. R.; Krauland, E. M.; Wittrup, K. D.; Belcher, A. M. *Langmuir* 2005, 21, 6929.
(5) Loening, A. M.; Fenn, T. D.; Wu, A. M.; Gambhir, S. S. *Protein Eng. Des. Sel.* 2006, 19, 391.
(6) Ma, N.; Yang, J.; Stewart, K. M.; Kelley, S. O. *Langmuir* 2007, 23, 12783.
(7) Zhao, X.; Gorelikov, I.; Musikhin, S.; Cauchi, S.; Sukhovatkin, V.; Sargent, E. H.; Kumacheva, E. *Langmuir* 2005, 21, 1086.
(8) van Sark, W. G. J. H. M.; Frederix, P. L. T. M.; Van den Heuvel, D. J.; Gerritsen, H. C.; Bol, A. A.; van Lingen, J. N. J.; Donegá, C. D. M.; Meijerink, A. *J. Phys. Chem. B* 2001, 105, 8281.
(9) Nel, A. E.; Madler, L.; Velegol, D.; Xia, T.; Hoek, E. M. V.; Somasundaran, P.; Klaessig, F.; Castranova, V.; Thompson, M. *Nat. Mater.* 2009, 8, 543.

Example 2

The luciferase-templated synthesis of PbS quantum dots (QDs) can be extended to other proteins and QDs. We tested the use of bovine serum albumin. (BSA) for the synthesis of different QDs including CdS, CdSe, and PbS QDs (See FIG. 2.1). Below is a summary of the synthetic conditions and QDs properties.

TABLE 1

Summary of synthetic conditions and QDs properties for BSA-templated QDs synthesis.

| QD | Protein | Precursors | Temperature | Reaction medium | QDs Emission maxima | QDs quantum yields |
|---|---|---|---|---|---|---|
| CdS | BSA | $CdCl_2$ and $Na_2S$ | Room temperature | $H_2O$ | 550 nm | 2% |
| CdSe | BSA | $CdCl_2$ and NaHSe | Room temperature | $H_2O$ | 580 nm | 8% |
| PbS | BSA | $Pb(Ac)_2$ and $Na_2S$ | Room temperature | 50 mM Tris (pH 7.5) or $H_2O$ | 980 nm | 3.5% |

BSA is an effective ligand and stabilizer for QD growth. Without BSA, only bulk insoluble materials were produced. FIG. 2.2 illustrates the photoluminescence spectra of BSA-QDs. (A) BSA-CdS QDs. (B) BSA-CdSe QDs. (C) BSA-PbS QDs.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

RLuc (*Renilla reniformis*)

SEQ ID NO: 1

MTSKVYDPEQRKRMITGPQWWARCKQMNVLDSFINYYDSEKHAENAVIF

LHGNAASSYLWRHVVPHIEPVARCIIPDLIGMGKSGKSGNGSYRLLDHY

KYLTAWFELLNLPKKIIFVGHDWGACLAFHYSYEHQDKIKAIVHAESVV

DVIESWDEWPDIEEDIALIKSEEGEKMVLENNFFVETMLPSKIMRKLEP

EEFAAYLEPFKEKGEVRRPTLSWPREIPLVKGGKPDVVQIVRNYNAYLR

ASDDLPKMFIESDPGFFSNAIVEGAKKFPNTEFVKVKGLHFSQEDAPDE

MGKYIKSFVERVLKNEQ

-continued

RLuc8 (*Renilla reniformis*)
(eight mutations include A55T, C124A, S130A, K136R, A143M, M185V, M253L, and S287L)

SEQ ID NO: 2

MTSKVYDPEQRKRMITGPQWWARCKQMNVLDSFINYYDSEKHAENAVIF

LHGNATSSYLWRHVVPHIEPVARCIIPDLIGMGKSGKSGNGSYRLLDHY

KYLTAWFELLNLPKKIIFVGHDWGAALAFHYAYEHQDRIKAIVHM

ESVVDVIESWDEWPDIEEDIALIKSEEGEKMVLENNFFVETVLPSKIMR

KLEPEEFAAYLEPFKEKGEVRRPTLSWPREIPLVKGGKPDVVQIVRNYN

AYLRASDDLPKLFIESDPGFFSNAIVEGAKKFPNTEFVKVKGLHFLQED

APDEMGKYIKSFVERVLKNEQ

SEQUENCE LISTING

<160> NUMBER OF SEQ ID NOS: 2

<210> SEQ ID NO 1
<211> LENGTH: 311
<212> TYPE: PRT
<213> ORGANISM: Renilla reniformis

<400> SEQUENCE: 1

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 2
<211> LENGTH: 311
<212> TYPE: PRT
<213> ORGANISM: Renilla reniformis

<400> SEQUENCE: 2

-continued

| | | | | | | | | | | | | | | |
|---|---|---|---|---|---|---|---|---|---|---|---|---|---|---|
| Met<br>1 | Thr | Ser | Lys | Val<br>5 | Tyr | Asp | Pro | Glu | Gln<br>10 | Arg | Lys | Arg | Met | Ile<br>15 | Thr |
| Gly | Pro | Gln | Trp<br>20 | Trp | Ala | Arg | Cys | Lys<br>25 | Gln | Met | Asn | Val | Leu<br>30 | Asp | Ser |
| Phe | Ile | Asn<br>35 | Tyr | Tyr | Asp | Ser | Glu<br>40 | Lys | His | Ala | Glu | Asn<br>45 | Ala | Val | Ile |
| Phe | Leu<br>50 | His | Gly | Asn | Ala | Thr<br>55 | Ser | Ser | Tyr | Leu | Trp<br>60 | Arg | His | Val | Val |
| Pro<br>65 | His | Ile | Glu | Pro | Val<br>70 | Ala | Arg | Cys | Ile | Ile<br>75 | Pro | Asp | Leu | Ile | Gly<br>80 |
| Met | Gly | Lys | Ser | Gly<br>85 | Lys | Ser | Gly | Asn | Gly<br>90 | Ser | Tyr | Arg | Leu | Leu<br>95 | Asp |
| His | Tyr | Lys | Tyr<br>100 | Leu | Thr | Ala | Trp | Phe<br>105 | Glu | Leu | Leu | Asn | Leu<br>110 | Pro | Lys |
| Lys | Ile | Ile<br>115 | Phe | Val | Gly | His | Asp<br>120 | Trp | Gly | Ala | Ala | Leu<br>125 | Ala | Phe | His |
| Tyr | Ala<br>130 | Tyr | Glu | His | Gln | Asp<br>135 | Arg | Ile | Lys | Ala | Ile<br>140 | Val | His | Met | Glu |
| Ser<br>145 | Val | Val | Asp | Val | Ile<br>150 | Glu | Ser | Trp | Asp | Glu<br>155 | Trp | Pro | Asp | Ile | Glu<br>160 |
| Glu | Asp | Ile | Ala | Leu<br>165 | Ile | Lys | Ser | Glu | Glu<br>170 | Gly | Glu | Lys | Met | Val<br>175 | Leu |
| Glu | Asn | Asn | Phe<br>180 | Phe | Val | Glu | Thr | Val<br>185 | Leu | Pro | Ser | Lys | Ile<br>190 | Met | Arg |
| Lys | Leu | Glu<br>195 | Pro | Glu | Glu | Phe | Ala<br>200 | Ala | Tyr | Leu | Glu | Pro<br>205 | Phe | Lys | Glu |
| Lys | Gly<br>210 | Glu | Val | Arg | Arg | Pro<br>215 | Thr | Leu | Ser | Trp | Pro<br>220 | Arg | Glu | Ile | Pro |
| Leu<br>225 | Val | Lys | Gly | Gly | Lys<br>230 | Pro | Asp | Val | Val | Gln<br>235 | Ile | Val | Arg | Asn | Tyr<br>240 |
| Asn | Ala | Tyr | Leu | Arg<br>245 | Ala | Ser | Asp | Asp | Leu<br>250 | Pro | Lys | Leu | Phe | Ile<br>255 | Glu |
| Ser | Asp | Pro | Gly<br>260 | Phe | Phe | Ser | Asn | Ala<br>265 | Ile | Val | Glu | Gly | Ala<br>270 | Lys | Lys |
| Phe | Pro | Asn<br>275 | Thr | Glu | Phe | Val | Lys<br>280 | Val | Lys | Gly | Leu | His<br>285 | Phe | Leu | Gln |
| Glu | Asp<br>290 | Ala | Pro | Asp | Glu | Met<br>295 | Gly | Lys | Tyr | Ile | Lys<br>300 | Ser | Phe | Val | Glu |
| Arg<br>305 | Val | Leu | Lys | Asn | Glu<br>310 | Gln | | | | | | | | | |

We claim the following:

1. A method of making a hybrid quantum dot/protein nanostructure, comprising:

introducing a first precursor compound to a bioluminescence protein in a solution, wherein the precursor compound includes a first atom, wherein the bioluminescence protein bonds to a plurality of first atoms to form first atom-bioluminescence protein complexes; and introducing a second precursor compound to the solution including the first atom-bioluminescence protein complexes to form the hybrid quantum dot/protein nanostructure, wherein the second precursor compound includes a second atom, wherein the first atom and the second atom interact to form a quantum dot core, wherein the quantum dot core has a plurality of bioluminescence proteins each bonded to a plurality of first atoms.

2. The method of claim 1, wherein the introduction of the first precursor compound and the introduction of the second precursor compound are conducted in the same reaction vessel.

3. The method of claim 1, wherein the introduction of the first precursor compound into the solution and the introduction of the second precursor compound into the solution are conducted without separating the first atom-bioluminescence protein complexes from the solution prior to introducing the second precursor compound into the solution.

4. The method of claim 1, wherein the first atom is selected from the group consisting of: Pb and Cd.

5. The method of claim 1, wherein the second atom is selected from the group consisting of: S and Se.

6. The method of claim 1, wherein the first atom is Pb and the second atom is S.

7. The method of claim 1, wherein the bioluminescence donor molecule is a Luciferase protein.

8. The method of claim 1, wherein the bioluminescence donor molecule is selected from a *Renilla* Luciferase protein, a mutated *Renilla* Luciferase protein, and a combination thereof.

9. The method of claim 1, wherein the bioluminescence donor molecule is a mutated Renilla Luciferase protein SEQ ID NO: 2.

10. The method of claim 1, wherein the core quantum dot is selected from the group consisting of: PbS, CdS, and CdSe.

11. The method of claim 1, wherein the core of the quantum dot is selected from: a IIB-VIA semiconductor, a IIIA-VA semiconductor, and a IVA-VIA semiconductor.

* * * * *

UNITED STATES PATENT AND TRADEMARK OFFICE
CERTIFICATE OF CORRECTION

PATENT NO. : 8,592,227 B2
APPLICATION NO. : 13/068174
DATED : November 26, 2013
INVENTOR(S) : Ma et al.

Page 1 of 1

It is certified that error appears in the above-identified patent and that said Letters Patent is hereby corrected as shown below:

In The Specification

At column 1, lines 17-20, in the paragraph entitled "Statement Regarding Federally Sponsored Research or Development", delete "This invention(s) was made with govermnent support under Grant No.: 1R01CA135294-01 and 1U54CA119367- 01 awarded by the National Cancer Institute. The government has certain rights in the invention(s )." and replace with --This invention was made with Government support under contracts CA119367 and CA135294 awarded by the National Institutes of Health. The Government has certain rights in the invention.--

Signed and Sealed this
Twenty-ninth Day of March, 2016

Michelle K. Lee
*Director of the United States Patent and Trademark Office*